United States Patent [19]

Hoskin

[11] Patent Number: 4,515,701

[45] Date of Patent: May 7, 1985

[54] LOW COST, BRINE TOLERANT SULFONATE AND SULFATE SURFACTANTS HAVING 1,3-DIHYDROCARBOXY-2-PROPYL HYDROPHOBIC TAILS

[75] Inventor: Dennis H. Hoskin, Lawrenceville, N.J.

[73] Assignee: Mobil Oil Corporation, New York, N.Y.

[21] Appl. No.: 583,513

[22] Filed: Feb. 24, 1984

Related U.S. Application Data

[62] Division of Ser. No. 413,591, Aug. 31, 1982, Pat. No. 4,446,079.

[51] Int. Cl.$^3$ .............................................. E21B 43/22
[52] U.S. Cl. ................................. 252/8.55 D; 166/275
[58] Field of Search ....................... 260/513 R, 513 B; 252/8.55 D; 166/275

[56] References Cited

U.S. PATENT DOCUMENTS

| | | | |
|---|---|---|---|
| 3,243,455 | 3/1966 | Pizzini et al. | 260/513 R |
| 3,592,796 | 7/1971 | Trapasso et al. | 260/513 R X |
| 4,018,278 | 4/1977 | Shupe | 252/8.55 D X |
| 4,110,228 | 8/1978 | Tyler et al. | 252/8.55 D |
| 4,463,806 | 8/1984 | Hurd | 252/8.55 D X |
| 4,468,335 | 8/1984 | Chen et al. | 252/8.55 D |
| 4,468,342 | 8/1984 | Chen | 252/8.55 D X |

FOREIGN PATENT DOCUMENTS

| | | | |
|---|---|---|---|
| 49-41415 | 8/1974 | Japan | 260/513 B |

*Primary Examiner*—Herbert B. Guynn
*Attorney, Agent, or Firm*—Alexander J. McKillop; Michael G. Gilman; James P. O'Sullivan, Sr.

[57] ABSTRACT

Novel sulfonate and sulfate surfactants which have low interfacial tension at high salinity, and their use in enhanced oil recovery are disclosed. These surfactants may be made from relatively inexpensive intermediates, such as monohydric alcohols and epichlorohydrin. These surfactants have 1,3-dihydrocarboxy-2-propyl hydrophobic tails linked by ethoxy linkages to sulfate or alkyl sulfonate moieties.

10 Claims, 4 Drawing Figures

FIG.1 INTERFACIAL TENSIONS AT DIFFERENT SALINITIES OF 0.1%

FIG. 2 INTERFACIAL TENSIONS AT DIFFERENT SALINITIES OF

FIG. 3 INTERFACIAL TENSIONS AT DIFFERENT SALINITIES OF 1:1

FIG. 4 OIL RECOVERY FROM BEREA SANDPACKS BY

LOW COST, BRINE TOLERANT SULFONATE AND SULFATE SURFACTANTS HAVING 1,3-DIHYDROCARBOXY-2-PROPYL HYDROPHOBIC TAILS

CROSS-REFERENCE TO RELATED APPLICATIONS

This Application is a division of copending Application Ser. No. 413,591 now U.S. Pat. No. 4,446,079. Copending U.S. patent application, Ser. No. 413,573, filed Aug. 31, 1982, in the name of Dennis H. Hoskin and Kirk D. Schmitt, relates to methods for making 1,3-dihydrocarboxy-2-propoxypolyethoxypropane sulfonate surfactants.

Copending U.S. patent application, Serial No. 373,550, filed Apr. 30, 1982, now U.S. Pat. No. 4,468,335, in the name of Catherine S. H. Chen and Albert L. Williams, describes (branched alkyl)-polyethoxypropane sulfonates and their use in enhanced oil recovery. This Chen et al. application is a continuation-in-part of U.S. patent applications Ser. No. 259,215 and Ser. No. 259,216 both filed Apr. 30, 1981, and both now abandoned.

Copending U.S. patent application Ser. No. 259,218, filed Apr. 30, 1981, now U.S. Pat. No. 4,442,042 in the name of Kirk D. Schmitt discloses a method for preparing alkylpolyethoxypropane sulfonates. This Schmitt application is, in turn, related to U.S. application, Ser. No. 96,947, filed Nov. 23, 1979, in the name of Catherine S. H. Chen, Kirk D. Schmitt and Albert L. Williams, entitled Method of Making Propane Sulfonates, now U.S. Pat. No. 4,267,123.

The above-mentioned U.S. patent applications and U.S. patent are expressly incorporated herein by reference.

BACKGROUND

This invention is directed to sulfonate and sulfate surfactants having 1,3-dihydrocarboxy-2-propyl hydrophobic tails, a process for their preparation and a process for their use in enhancing the secondary or tertiary recovery of oil from subterranean oil deposits or reservoirs, particularly from high salinity reservoirs. In particular, these sulfonates and sulfates are suitable as single component surfactants in continuous chemical flooding techniques.

In the recovery of oil from oil bearing deposits it is generally possible to recover only a portion of the original oil by so called "primary methods" which utilize only the natural forces present in the reservoir or deposit. Thus a variety of supplemental techniques have been employed in order to increase the recovery of oil from these subterranean reservoirs. The most widely used supplemental recovery technique is water flooding which involves injection of water into an oil bearing reservoir. However, there are problems associated with the water flooding technique and water soluble surfactants have generally been required to be used for this process to be completely successful. Thus the LTWF (Low Tension Water Flood) method using surfactants which function in low salinity (less than 3 percent) is well known. However, it has been found that preflushing the reservoirs with fresh or low salinity water to reduce the salinity so that the low salinity surfactants of the prior art may be used is not always effective, or, the preflushing is effective only for a short duration and the salinity of the fresh water increases over a period of time since it is in contact with reservoir rocks and clays. Either event renders the low salinity surfactants useless and therefore it is of vital importance to have a surfactant which functions at the salinity of the connant water to negate the necessity of preflushing.

Developments for using surfactants to enhance oil recovery may be categorized according to essentially two different concepts. In the first, a solution containing a low concentration of surfactants is injected into the reservoir. The surfactant is dissolved or dispersed in either water or oil. Large pore volumes (about 15-60% or more) of the liquid are injected into the reservoir to reduce interfacial tension between oil and water and thereby increase oil recovery. Specific relationships exist between interfacial tensions of the oil against the flooding media and the percentage recovery obtained by flooding, i.e., the efficiency of flooding increases as the interfacial tension decreases. Oil may be banked with the surfactant solution process but residual oil saturation at a given position in the reservoir will only approach zero after passage of large volumes of this flooding media.

In the second process, a relatively small pore volume (about 3-20%) of a higher concentration surfactant liquid is injected into the reservoir. The high concentration surfactant liquids displace both oil and water and readily displace all the oil contacted in the reservoir. As the high concentration slug moves in the reservoir, it is diluted by formation flood and the process reverts to a low concentration flood; Enhanced Oil Recovery, Van Poolen & Associates, 1980, Tulsa Oklahoma.

Aqueous surfactant liquids for injecting into reservoirs contain two essential components, namely, water and surfactant. An optional third component may be a hydrocarbon. Such three component mixtures of water, surfactant and hydrocarbon may be in the form of a water-external micellar dispersion as discussed in the Jones U.S. Pat. No. 3,506,071. A cosurfactant fourth component (usually alcohol) can be added. Electrolytes, normally inorganic salts, form a fifth component that may be used.

Work is still in progress in the laboratory and in the field to select the optimum method of injecting surfactant to improve oil recovery. The best process for a specific reservoir is the one which has the potential to provide the greatest efficiency and yield regardless of the concentration level of the surfactant. The chemical system, however, to be efficient must be tailored to the specific reservoir.

The prior art with respect to the use of surfactant polymer floods to recover oil from reservoirs has disclosed that for a given amount of surfactant, a small slug process with a high surfactant concentration is more efficient than a large slug process with a low surfactant concentration. The former produces oil earlier and takes a smaller number of pore volumes to complete oil production. This is a favorable condition. However, it has become evident that fluid dispersion and mixing take place in the reservoirs and the slug intake routine cannot be maintained. Deterioration of the surfactant and the mobility control slug can lead to process failure or at least a reduction in process efficiency. For heterogeneous reservoirs where fluid dispersion and mixing takes place to a greater extent it is desirable if not vital to have a continuous flooding process with a surfactant which can move oil even at very low concentrations.

There has now been discovered certain novel surfactants and their use in a continuous flooding process wherein low concentrations of the novel surfactant alone can be used to increase the oil production during secondary water flooding processes or to recover residual tertiary oil where the reservoirs already have been water flooded.

SUMMARY OF THE INVENTION

The present invention relates to novel sulfonate and sulfate surfactants having 1,3-dihydrocarboxy-2-propyl hydrophobic tails, processes for their preparation and processes for their use, particularly at low concentrations in enhanced oil recovery. The enhanced oil recovery process is especially adaptable to high salinity reservoirs, e.g., reservoirs having a salinity of from about 4 to 30%.

These sulfonate and sulfate surfactants, in amount effective for the intended purpose can be used as a single component surfactant without the addition of any other component or cosurfactant. However, it may be desirable to use mixtures of two or more of the branched surfactants described herein, or to use the surfactant in combination with a sacrificial agent such as lignin sulfonate.

DETAILED DESCRIPTION

Surfactants of this invention may have the formula:

(VI)

where $R_1$ and $R_2$ are the same or different and are $C_1$–$C_{15}$ hydrocarbyl, $R_3$ is $C_{0-5}$ alkyl, M is a cation and n is a rotational number (e.g., including fractions) from 2 to 6. Preferably, $R_1$ and $R_2$ are $C_1$–$C_{10}$ alkyl, especially, $C_4$–$C_{10}$ alkyl. $R_1$ and $R_2$ together preferably contain at least 7 carbon atoms. Preferably, n is a rational number from 2 to 4.

In addition to alkyl groups, suitable hydrocarbyl groups for use as $R_1$ and $R_2$ include, e.g., aryl, arylalkyl, and alkylaryl.

It is noted that when $R_3$ is $C_0$alkyl (i.e., $R_3$ is absent), the surfactant of formula (VI) is a sulfate. When $R_3$ is $C_{1-5}$alkyl, the surfactant of formula (VI) is a sulfonate, preferably $R_3$ is $CH_2CH_2CH_2$.

M is preferably a monovalent cation. Examples of such monovalent cations include ions of alkali metals and nitrogenous bases. Where M is an alkali metal ion, it may be sodium or potassium. Various nitrogenous bases, including ammonium or quaternary amines, may be employed. Representative alkylammonium ions include methylammonium, ethylammonium, and normal or isopropylammonium ions, and examples of alkanolammonium ions include monoethanolammonium and triethanolammonium ions.

The surfactants of the present invention produce ultralow interfacial tensions over a wide salinity range at low concentration on Berea sandpacks. A desired salinity window can, within limits, be achieved by varying the degree of ethoxylation of these to tune the hydrophobe/hydrophile ratio. The synthesis of these surfactants is accomplished from relatively inexpensive starting materials by conventional technology. An important feature of this synthesis is the utilization of epichlorohydrin as a low-cost method for achieving desirable two-tailed intermediates for further functionalization.

An example of this synthesis may be illustrated as follows:

The primary advantage of this route is that appropriately sized two-tailed alcohols (formula III) are made from inexpensive commercially available smaller alcohols. This procedure is generally described in the Blake U.S. Pat. No. 2,932,616, the entire disclosure of which is expressly incorporated herein by reference.

EXAMPLE 1

Following the above procedure, a two-tailed alcohol of formula III, where $R_1=R_2=CH_2CH(C_2H_5)C_4H_9$, was made in 63% yield by the reaction of a sodium alkoxide (from 2-ethylhexanol and sodium metal) with epichlorohydrin. The alcohol of formula III was then partially metallized (less than or equal to 50%) with sodium metal and ethoxylated by sparging ethylene oxide into the hot (125°–150° C.) alcohol-alkoxide mixture. After the desired degree of ethoxylation was attained (as monitored by weight uptake), the intermediates were further functionalized to the surfactants of formula V by full metalization with Na followed by the addition of an approximately equimolar portion of propane sultone. Although other adducts have been synthesized and characterized (e.g., where $R_1=R_2=$n-hexyl) currently the best characterized member of this surfactant family is according to formula V, where $R_1=R_2=CH_2CH(C_2H_5)C_4H_9$ and n=3.2. This surfactant was isolated in 67% overall yield from the corresponding alcohol of formula III, including a rigorous preparative reverse phase HPLC purification step. During purification, the product where n=3.2 was collected in two cuts having differing average ethoxylation (n=2.4 and 3.6, respectively, by $^{13}$C-NMR integration). Because this procedure gave products where n=2.4 and 3.6 of limited dispersity, these products were also mixed 1:1 (where n=3.0) for characterization purposes. The spinning drop method was used to determine interfacial tensions between West Burkburnett (WBB) oil and surfactant-brine mixtures. This spinning drop method is described by Wade in Adsorption at Interfaces, ACS Symp. #8, pp. 234–247 (1975).

Figure 1:
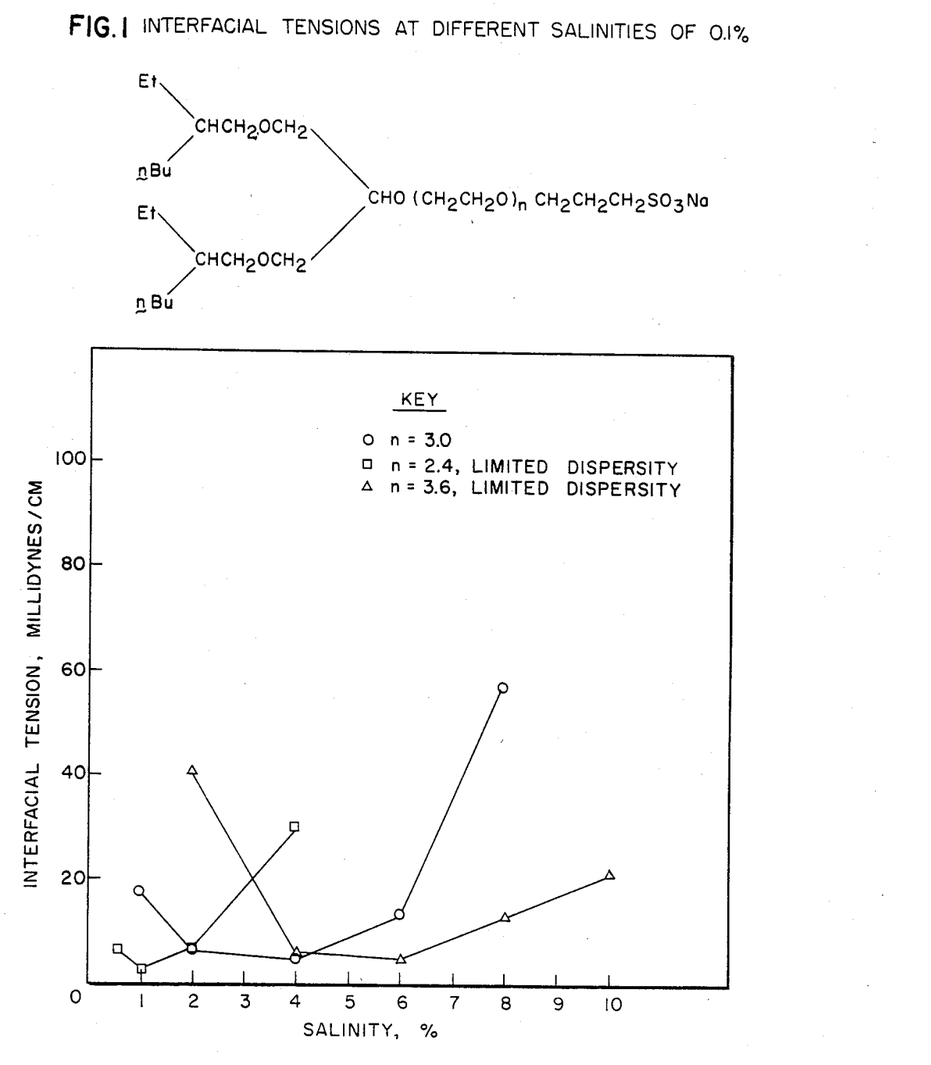
FIGS. 1–3 show graphs of interfacial tension of surfactants according to the present invention at different salinities.
Figure 2:
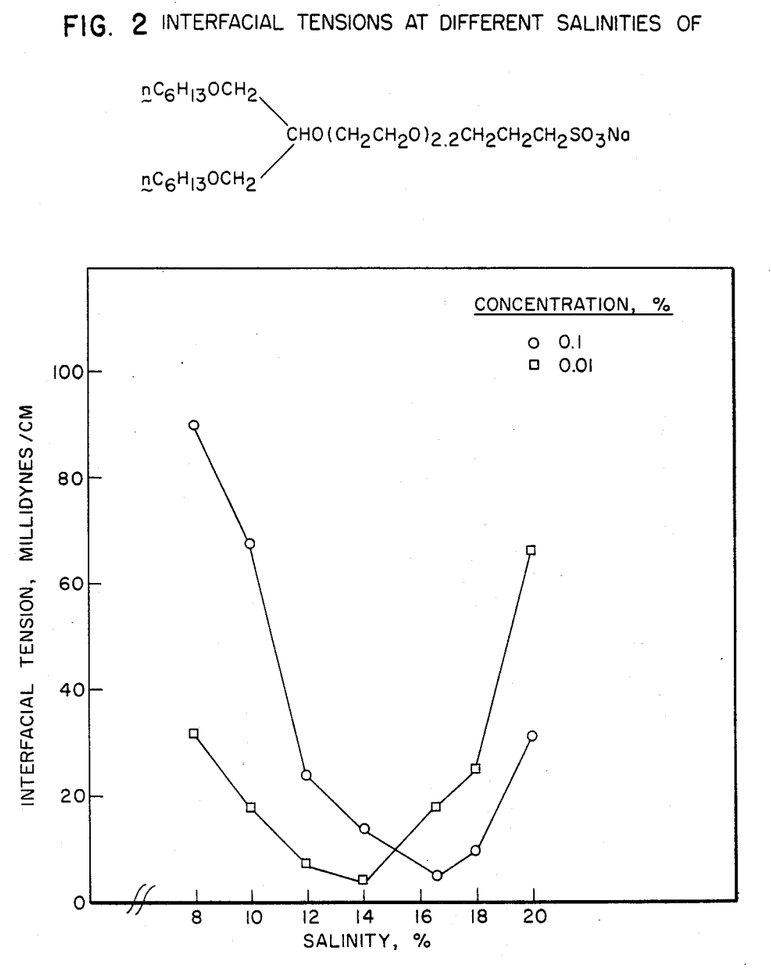

The brine used contained $Na^+$, $Ca^{2+}$, and $Mg^{2+}$ in the ratio found in WBB brine. WBB brine has 16.6% by weight of total salt and was prepared by adding to water 13.2% by weight $NaCl_2$, 3.47% by weight $CaCl_2.2H_2O$ and 1.53% by weight $MgCl_2.6H_2O$. Interfacial tension data are summarized in Tables I–V and depicted in FIGS. 1–3. This data was obtained in the following manner.

A spinning drop Interfacial Tensiometer was used. Measurements, against a crude oil, were made after 30 minutes spinning at 10 to 14 msec., or longer, or until no more change in the drop took place. The width of the drop was then measured. The interfacial tension was calculated according to the below equation when the length of the drop was $\geq 4$ times its diameter.

$$IFT = \frac{9.8696 \times 10^6 \times \Delta d \times \left[\frac{Dm}{66.6}\right]^3}{P^2}$$

where
IFT = Interfacial Tension, Dynes/cm
$\Delta d$ = difference in density between oil and brine
Dm = diameter of oil drop (cm) measured from photograph
P = spinning speed, msec/revolution

TABLE I
INTERFACIAL TENSIONS AT DIFFERENT SALINITIES

| WBB Salinity, % | IFT Against WBB Oil, dynes/cm Surf. Conc., % | | |
|---|---|---|---|
| | 0.1 | 0.01 | 0.001 |
| 8 | 0.0565 | — | — |
| 6 | 0.0116 | 0.0334 | 0.297 |
| 4 | 0.0052 | 0.0071 | 0.0138 |
| 2 | 0.0058 | 0.0055 | Too High |
| 1 | 0.0169 | — | — |

Too High: Cannot be measured by the Spinning Drop method.

TABLE II
INTERFACIAL TENSIONS AT DIFFERENT SALINITIES

| WBB Salinity, % | IFT Against WBB Oil, dynes/cm Surf. Conc., % | | |
|---|---|---|---|
| | 0.1 | 0.01 | 0.001 |
| 4 | 0.0296 | 0.0406 | 0.078 |
| 2 | 0.0064 | 0.011 | Too High |
| 1 | 0.0017 | 0.0049 | Too High |
| 0.5 | 0.0068 | 0.0017 | Too High |

Too High: Cannot be measured by the Spinning Drop method.

TABLE III
INTERFACIAL TENSIONS AT DIFFERENT SALINITIES

Et\
  \CHCH₂OCH₂
nBu/         \
              CHO—(CH₂CH₂O)₃.₆CH₂CH₂CH₂SO₃Na
Et\          /
  \CHCH₂OCH₂
nBu/

| WBB Salinity, % | IFT Against WBB Oil, dynes/cm Surf. Conc., % | | |
|---|---|---|---|
| | 0.1 | 0.01 | 0.001 |
| 10 | 0.0188 | — | — |
| 8 | 0.0126 | 0.0132 | 0.0209 |
| 6 | 0.0045 | 0.0023 | Too High |
| 4 | 0.0071 | 0.0109 | 0.0072 |
| 2 | 0.0408 | 0.0287 | Too High |

Too High: Cannot be measured by the Spinning Drop method.

TABLE IV
INTERFACIAL TENSIONS AT DIFFERENT SALINITIES

| WBB Salinity, % | IFT Against WBB Oil, dynes/cm Surf. Conc., % | | |
|---|---|---|---|
| | 0.1 | 0.01 | 0.001 |
| 20 | 0.0297 | 0.0663 | Too High |
| 18 | 0.0088 | 0.025 | " |
| 16.6 | 0.0041 | 0.0174 | " |
| 14 | 0.0116 | 0.0038 | " |
| 12 | 0.0226 | 0.0071 | 0.106 |
| 10 | 0.0677 | 0.0174 | Too High |
| 8 | 0.0904 | 0.0310 | " |
| 6 | 0.151 | — | — |
| 4 | 0.258 | — | — |

Too High: Cannot be measured by the Spinning Drop method.

TABLE V
INTERFACIAL TENSIONS AT DIFFERENT SALINITIES OF 1:1

$$\begin{array}{c} Et \\ \phantom{xx}\diagdown \\ \phantom{xxxx}CHCH_2OCH_2 \\ \diagup \phantom{xxxxxxxxx}\diagdown \\ nBu \phantom{xxxxxxxxxxx} CHO(CH_2CH_2O)_{3.0}CH_2CH_2CH_2SO_3Na: \\ Et \phantom{xxxxxxxxxx}\diagup \\ \phantom{xx}\diagdown \phantom{xxxxx}\diagup \\ \phantom{xxxx}CHCH_2OCH_2 \\ \diagup \\ nBu \end{array}$$

$$\begin{array}{c} nC_6H_{13}OCH_2 \\ \phantom{xxxxxxx}\diagdown \\ \phantom{xxxxxxxxxxx}CHCH_2O(CH_2CH_2O)_{2.2}CH_2CH_2CH_2SO_3Na \\ \phantom{xxxxxxx}\diagup \\ nC_6H_{13}OCH_2 \end{array}$$

| | IFT Against WBB Oil, dynes/cm Surf. Conc., % | | |
|---|---|---|---|
| WBB Salinity, % | 0.1 | 0.01 | 0.001 |
| 18 | 0.0607 | — | — |
| 16.6 | 0.0411 | 0.107 | Too High |
| 14 | 0.0227 | 0.0972 | " |
| 12 | 0.0229 | 0.046 | " |
| 10 | 0.0097 | 0.0416 | " |
| 8 | 0.0072 | 0.0228 | 0.106 |
| 6 | 0.0294 | 0.0061 | 0.0961 |
| 4 | 0.0534 | 0.0061 | 0.138 |
| 2 | 0.0899 | 0.0142 | Too High |

Too High: Cannot be measured by the Spinning Drop method.

Figure 3:
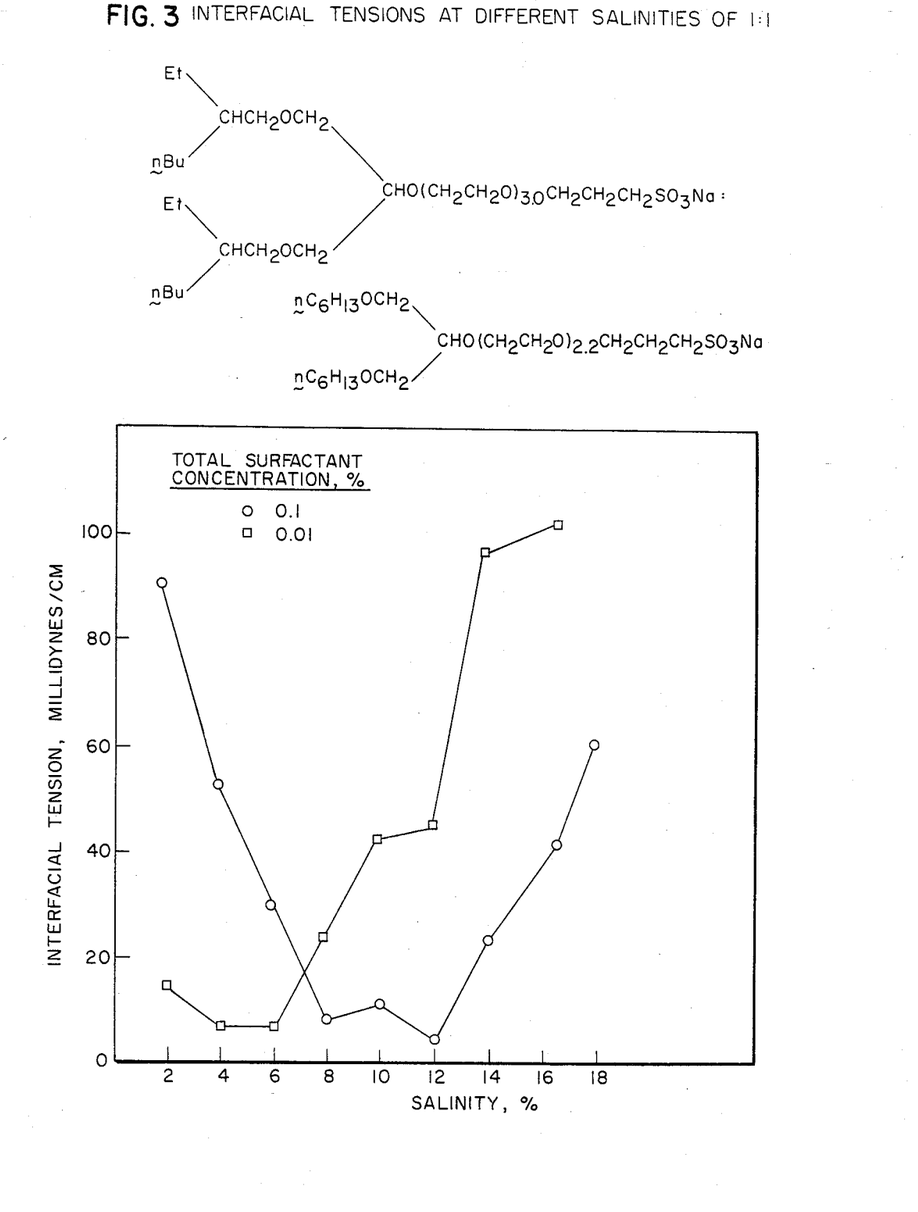

These data indicate that compounds of the present invention produce ultralow IFT's in brine containing divalent cations and suggest that varying the hydrophobe/hydrophile ratio by means of ethoxylation tunes the brine tolerance of the resultant surfactant (see FIG. 1) with acceptable "windows". Mixing surfactants with different hydrophobic tails changes the location of the brine tolerant window as a 1:1 mixture of a surfactant where $R_1=R_2=CH_2CH(C_2H_5)C_4H_9$ and n=3.0 (tolerant to 2–6% WBB brine) and a surfactant where $R_1=R_2=$n-hexyl and n=2.2 (tolerant to 14–18% WBB brine) produces ultralow IFT's at 8–12% WBB brine (0.1% concentration) (FIG. 3).

EXAMPLE 2

Berea sandpack tube runs were performed according to the following procedure.

A 6'×½" (o.d.) glass column was packed with Berea sand (40 to 325 mesh, typically 155 g). After evacuation the dry sandpack column was filled (ca. 35 ml) with West Burkburnett (WBB) brine of the appropriate salinity (that of the subsequent oil recovery experiment). The brine then was displaced by WBB crude oil until brine production ceased. Secondary oil recovery was simulated next by flushing with WBB brine of the appropriate salinity until oil production ended. The remaining oil (in a typical example 9.2 ml or 26.9 percent saturation) was the target of a tertiary oil recovery simulation experiment.

Tertiary oil recovery was effected by injecting 1 PV 0.3% sodium 1,3-bis[(2-ethylhexyl)oxy]-2-propoxypolyethyleneoxypropanesulfonate of limited polydispersity with 1% lignosulfonate sacrificial chemical and 500 ppm polysaccaride mobility control in either 2 or 4% WBB brine. This was followed by 0.3 PV of 500 ppm polysaccaride then 0.2 PV of 250 ppm polysaccaride in the appropriate brine and then continually with the same brine.

Figure 4:
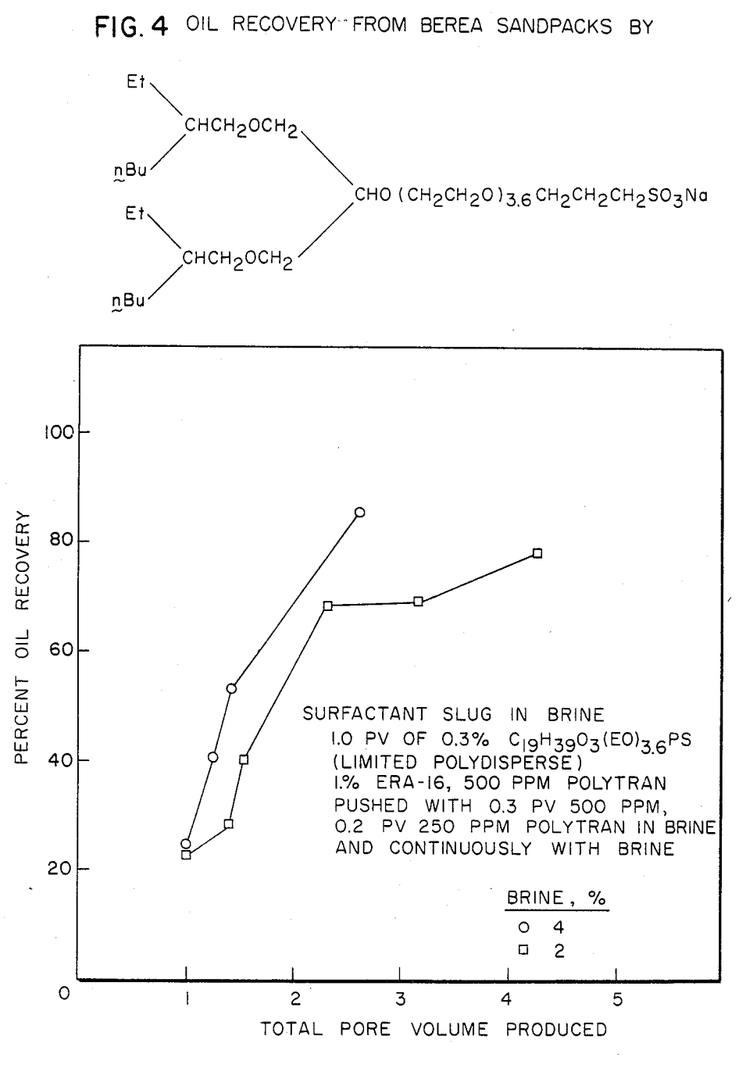
FIG. 4 shows a graph of oil recovery from Berea sandpacks by a surfactant according to the present invention.

The results are summarized in FIG. 4. The limited dispersity surfactant where $R_1=R_2=CH_2CH(C_2H_5)C_4H_9$ and n=3.6 recovered 85% of the oil in 4% WBB brine.

The surfactants of this invention generally have their minimum interfacial tension at salinities of less than about 30%, typically at about 4 to 28%. Indeed, the surfactants can be tailored for use in particular salinity ranges by varying the overall chain length of the alkoxy radicals (defined as "$R_1O$ and $R_2O$" above).

As indicated previously, the surfactants of this invention can be prepared by methods which in themselves are known in the art as illustrated in Example 1. One such method involves the reaction of an alkali metal salt of the branched alcohol of formula IV with propane sultone. This route provides a convenient laboratory synthesis and gives high yields but is not desirable on a large scale for several reasons. Foremost among them are the facts that (1) such a reaction requires multistep synthesis and purification of propane sultone (2) propane sultone is expensive to purify and its overall yield of 80–90% limits the yield in the preparation of propane sulfonates and (3) propane sultone is a known carcinogen. Therefore, processes involving the use of propane sultone must utilize expensive controls to minimize worker exposure but despite such controls its use will always engender some risk.

An alternative method of synthesis which has potential advantages on a commercial scale without the use of propane sultone can be conducted in accordance with the following reaction sequence.

(I) $RO(C_2H_4O)_nH + NaOH + CH_2=CH-CH_2X \longrightarrow$ $RO(C_2H_4O)_nCH_2CH=CH_2 + NaX$ (II) $RO(C_2H_4O)_nCH_2CH=CH_2 + NaHSO_3 \longrightarrow$ $RO(C_2H_4O)_nCH_2CH_2CH_2SO_3Na$ $R_1$, $R_2$ and n are as defined above and X is halogen or aryl sulfonates (e.g., tosylate).

Where R is such that the allyl ether product of reaction (I) has a solubility in water of less than 0.5% the process can be conducted in two steps in a single reactor without isolation of intermediates in almost 100% yield by control of reaction conditions in steps (I) and (II). Step (I) can be carried out in a completely aqueous system if about 50% NaOH is used as the base and if close contact between the water insoluble allyl halide and alcohol is brought about by inclusion of a certain minimum amount of desired sulfonate final product in the reaction vessel. At the end of the reaction any excess allyl chloride is easily distilled from the reactor. It needs not be dried but may be recycled directly, nor must it be separated from an organic solvent since no organic solvent is used.

The preparation of allyl ethers by the reaction of sodium or sodium methoxide with the alcohol followed by reaction with allyl chloride all in an organic solvent such as toluene or tetrahydrofuran (the Williamson ether synthesis) is well known and may be found in many standard textbooks on organic chemistry.

The reaction of NaHSO$_3$ with simple olefins, step (II), has been much studied. The literature teaches that for simple water-soluble olefins or olefins which can be made soluble by the addition of small amounts of alcohols, all that is required for high conversions to the desired products are conditions in which all reagents are dissolved in a single phase.

In the present method of preparation the corresponding ether intermediates do not behave this way. Conditions may be found in which all the reagents are dissolved in a single phase in alcohol and water and yet conversion will not exceed 40 or 50%. However, when a minor amount of propane sulfonate product is present in the reaction medium the conversion may be as high as 90% or more. Accordingly, it is advantageous to recycle part of the sulfonate final product of the reaction so that it is present during reaction. In general, the propane sulfonate product is present in a molar ratio of 1:1 to about 1:10 based on the allyl ether.

A convenient alternative to reaction of high molecular weight alcohols with metallic sodium is their reaction with sodium methoxide as exemplified by the following reaction sequence.

In this reaction sequence, the intermediate may be ethoxylated directly (i.e., omitting the final neutralization step with acid as depicted above) to give further intermediates in accordance with reaction sequences for preparing compounds of the present invention.

EXAMPLE 3

In accordance with the general procedure of the above reaction sequence, 13.3 g Na (.578 mole) were dissolved in 20 min in 100 ml CH$_3$OH and added to 75 g (.577 mole) 2-ethylhexanol in 175 ml dry, refluxing xylene under N$_2$. The mixture was fractionally distilled until the overhead reached 125°, the heat removed, and 25.9 g (.280 mole) epichlorohydrin added over 15 min. A vigorous exothermic reaction was noted. The mixture was refluxed 20 min, cooled to room temperature, diluted with 500 ml ethyl ether, washed with water, saturated brine, the solvents evaporated in vacuo and the material distilled to give 70.4 g (61%) pale yellow oil, bp 110°–150°/0.05 mm whose gas chromatograph shows two peaks at 58 sec and 192 sec in ratio 4:96 on a 6'× 10% carbowax column at 230° C. C-13 NMR shows the expected peaks at 74.8, 72.4, 69.5, 39.8, 30.7, 29.2, 24.1, 23.1, 14.0, and 11.1 ppm relative to TMS. The presence of a small peak at 58.9 ppm probably indicates the 4% impurity (58 sec GC retention time) is:

$$\begin{array}{c} CH_3OCH_2 \\ | \\ CHOH \\ | \\ CH_3OCH_2 \end{array}$$

In summary, advantages of the surfactants according to the present invention are as follows:
  (a) They can be propane sulfonates which are hydrolytically stable.
  (b) They are tolerant to high brine (including divalent cations).
  (c) They have a wide window of brine tolerance.
  (d) They can be made inexpensively by conventional technology.
  (e) The hydrophobic portion of the molecule is easily made monoisomeric.

What is claimed is:

1. A fluid for the secondary recovery of oil comprising brine and a surfactant which is a compound of the formula where R$_1$ and R$_2$ are the same or different and are C$_1$–C$_{15}$ hydrocarbyl, R$_3$ is C$_{0-5}$ alkyl, M is a cation and n is a rational number from 2 to 6 said surfactant being present in said brine in an amount sufficient to enhance secondary or tertiary recovery of oil from subterranean reservoirs.

2. A fluid according to claim 1, wherein R$_1$ and R$_2$ are C$_4$–C$_{10}$ alkyl, R$_3$ is CH$_2$CH$_2$CH$_2$ and n is a rational number from 2 to 4.

3. A fluid according to claim 2, wherein R$_1$ and R$_2$ are —CH$_2$CH(C$_2$H$_5$)C$_4$H$_9$, M is NA and n is 3.2.

4. A fluid according to claim 2, wherein R$_1$ and R$_2$ are n-hexyl, M is Na, and n is 2.2.

5. A fluid according to claim 2, wherein R$_1$ and R$_2$ are —CH$_2$CH(C$_2$H$_5$)C$_4$H$_9$, M is Na and n is 2.4.

6. A fluid according to claim 2, wherein R$_1$ and R$_2$ are —CH$_2$CH(C$_2$H$_5$)C$_4$H$_9$, M is Na and n is 3.6.

7. A fluid according to claim 2, wherein R$_1$ and R$_2$ are —CH$_2$CH(C$_2$H$_5$)C$_4$H$_9$, M is Na and n is 3.0.

8. A process for recovering oil from a subterranean oil reservoir having one or more production wells and one or more injection wells in contact with said oil reservoir, said process comprising
  contacting said oil reservoir with an aqueous medium including a compound of the formula where $R_1$ and $R_2$ are the same or different and are $C_1$-$C_{15}$ hydrocarbyl, $R_3$ is $C_{0-5}$ alkyl, M is a cation and n is a rational number from 2 to 6 at a concentration effective to increase oil production from said production well during secondary water flooding or to recover residual tertiary oil when the oil reservoir has been previously flooded.

9. A process according to claim 8, wherein said reservoir has a salinity of from about 4 to about 30%.

10. A process according to claim 9, wherein $R_1$ and $R_2$ are $C_4$-$C_{10}$ alkyl, $R_3$ is $CH_2CH_2CH_2$, M is Na and n is a rational number from 2 to 4.

* * * * *